United States Patent
Wong et al.

(10) Patent No.: US 8,222,427 B2
(45) Date of Patent: Jul. 17, 2012

(54) BISULFITE PURIFICATION OF AN ALPHA-KETO AMIDE

(75) Inventors: George S. K. Wong, Summit, NJ (US);
Jeonghan Park, Whippany, NJ (US);
Tetsuo Iwama, Scotch Plains, NJ (US);
Anantha R. Sudhakar, Fremont, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 200 days.

(21) Appl. No.: 12/518,736

(22) PCT Filed: Dec. 13, 2007

(86) PCT No.: PCT/US2007/025520
§ 371 (c)(1),
(2), (4) Date: Sep. 10, 2009

(87) PCT Pub. No.: WO2008/076316
PCT Pub. Date: Jun. 26, 2008

(65) Prior Publication Data
US 2009/0326244 A1    Dec. 31, 2009

Related U.S. Application Data

(60) Provisional application No. 60/875,195, filed on Dec. 15, 2006.

(51) Int. Cl.
*C07D 209/00*    (2006.01)
(52) U.S. Cl. ....................................... 548/452
(58) Field of Classification Search ............... 548/452
See application file for complete search history.

(56) References Cited

U.S. PATENT DOCUMENTS

| 7,326,795 B2 * | 2/2008 | Sudhakar et al. ............ 548/515 |
| 7,605,275 B2 * | 10/2009 | Chen et al. .................... 549/299 |
| 2003/0216325 A1 | 11/2003 | Saksena et al. |
| 2005/0059800 A1 * | 3/2005 | Sudhakar et al. ............ 530/331 |

FOREIGN PATENT DOCUMENTS

| WO | WO02/022459 | 3/2002 |
| WO | WO2005/107745 | 11/2005 |
| WO | WO 2006/076415 A2 | 7/2006 |

OTHER PUBLICATIONS

Marchs's Advanced Organic Chemistry, 5th Edition (2001), p. 1185).*
Dauben et al. Organic Syntheses, Coll. vol. 4, p. 221—(1963) and March's Advanced Organic Chemistry, 5th Edition (2001), p. 1185.*
International Search Report for International Application No. PCT/US2007/025520 filed Dec. 13, 2007; mail date Aug. 13, 2008; 5 pages; published as WO 2008/076316 on Jun. 26, 2008 with Search Report.

* cited by examiner

*Primary Examiner* — Yong Chu
*Assistant Examiner* — Valerie Rodriguez-Garcia
(74) *Attorney, Agent, or Firm* — Julie M. Lake; Sheldon O. Herber

(57) ABSTRACT

This disclosure relates to novel processes useful in the purification of keto-amide, ketone and aldehyde compounds, which are useful as inhibitors of the hepatitis C virus (HCV) NS3 protease and have application in the treatment of conditions caused by HCV. The processes of this disclosure relate to purification via a bisulfite adduct. In particular, this disclosure relates to processes useful in the purification of the keto-amide compound of Formula I, (1R,5S)-N-[3-amino-1-(cyclobutylmethyl)-2,3-dioxopropyl]-3-[2(S)-[[[(1,1-dimethylethyl)amino]carbonyl]-amino]-3,3-dimethyl-1-oxobutyl]-6,6-dimethyl-3-azabicyclo[3.1.0]hexan-2(S)-carboxamide:

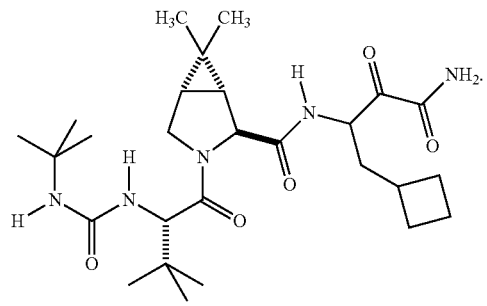

17 Claims, No Drawings

BISULFITE PURIFICATION OF AN ALPHA-KETO AMIDE

CROSS-REFERENCE TO RELATED APPLICATIONS

This application is entered into national stage examination under 35 U.S.C. 371 and stems from International patent application No. PCT US2007/025520 filed in the U.S. PCT receiving office on Dec. 13, 2007, which claims the priority of U.S. provisional patent application Ser. No. 60/875,195 filed Dec. 15, 2006. Each of the aforementioned PCT and Provisional applications is incorporated by reference herein in its entirety.

FIELD OF THE INVENTION

The present invention relates to a process for the purification of an alpha-keto amide via the formation of a bisulfite adduct, for example, the purification of the alpha-keto amide (1R,5S)-N-[3-amino-1-(cyclobutylmethyl)-2,3-dioxopropyl]-3-[2(S)-[[[(1,1-dimethylethyl)amino]carbonyl]amino]-3,3-dimethyl-1-oxobutyl]-6,6-dimethyl-3-azabicyclo[3.1.0]hexan-2(S)-carboxamide, an HCV protease inhibitor.

BACKGROUND

Identification of any publication in this section or any section of this application is not an admission that such publication is prior art to the present invention.

Hepatitis C virus (HCV) is a (+)-sense single-stranded RNA virus that has been implicated as the major causative agent in non-A, non-B hepatitis; an HCV protease necessary for polypeptide processing and viral replication has been identified. U.S. Pat. No. 7,012,066 discloses a genus of HCV protease inhibitor compounds that includes the compound of Formula I, (1R,5S)-N-[3-amino-1-(cyclobutylmethyl)-2,3-dioxopropyl]-3-[2(S)-[[[(1,1-dimethylethyl)amino]-carbonyl]amino]-3,3-dimethyl-1-oxobutyl]-6,6-dimethyl-3-azabicyclo[3.1.0]hexan-2(S)-carboxamide.

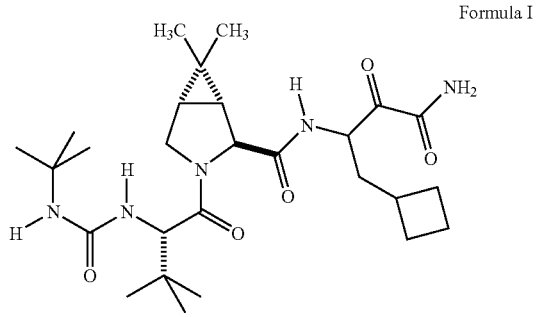

Formula I

US2005/0059800, published Mar. 17, 2005, discloses a process for preparing the compound of Formula I and discloses a bisulfite adduct of Formula I which can be used to provide the compound in a pure form in accordance with the methods taught in *Advanced Organic Chemistry*, 4th ed., Jerry March Ed., John Wiley and Sons, 1972.

US2005/0020669, filed Jan. 27, 2005, discloses processes for preparing an intermediate useful in preparing the compound of Formula I. Methods for preparing diastereomers of the compound of Formula I are disclosed in US2005/0249702, filed Nov. 10, 2005. Published US Patent Application No. 2007/0149459, filed Nov. 13, 2006, discloses oxidation processes for preparing the compound of Formula I.

Purification of the compound of Formula I is difficult for several reasons. The compound Formula I is an alpha-keto amide that is unstable and forms dimers, especially under basic conditions. Also, the compound of Formula I is amorphous, thus it does not crystallize and precipitation does not improve the purity of the solid.

Previously published procedures for preparing the compound of Formula I resulted in about 63 to about 98.5% purity.

Historically, aldehydes and ketones have been purified by preparing their bisulfite adduct. Bisulfite purification of these types of compounds was performed through isolation of a solid bisulfite adduct intermediate from aqueous alcoholic solution by filtration. Regeneration of an aldehyde or ketone from an isolated bisulfite adduct is accomplished using a base or a strong acid. Examples appearing in the literature of regeneration using bases includes: $Na_2CO_3$ in *Org. Synthesis Coll.* Vol. 4, 903 (1963); NaOH in WO 2006/074270 A2; and $K_2CO_3$ in *Tetrahedron Lett.*, 45, 3219 (2004). Examples of regeneration using acids include: $H_2SO_4$ in *J. Am. Chem. Soc.*, 70, 1748 (1948); and HCl in WO 99/57123.

For the preparation of a purified product, isolation of an intermediate solid bisulfite adduct is not preferred since filtration of the adduct is required. In addition, base regeneration of the adduct to yield the substrate is not appropriate in those cases wherein the regenerated product is unstable in basic conditions, for example, where the regenerated product is the compound of Formula I. When acid conditions are used to regenerate the substrate compound from a bisulfite adduct, generally strongly acidic conditions and heating are necessary (see references above).

Published international application no. WO 99/57123 reports using non-alcoholic solvent in a process for forming a bisulfite adduct, however the process required isolation of a solid bisulfite adduct and regeneration the substrate from the adduct using NaOH.

A non-aqueous method for regeneration of a substrate from the corresponding bisulfite adduct was reported in *J. Org. Chem.*, 64, 5722 (1999) as a means to overcome side-reactions such as degradation and hydrolysis during regeneration of aldehyde/ketone with a base or an acid. In this method, trimethylsilyl chloride (TMSCl) or its equivalent was employed in acetonitrile. During the process $TMS_2O$, NaCl, $SO_2$ and HCl were generated as co-products when TMSCl was used. Removal of the co-products required the process steps of filtration (for NaCl), aqueous work-up (for NaCl and excess TMSCl) and distillation (for $TMS_2O$), which requires use of a high boiling solvent. Regeneration of aldehydes from the corresponding bisulfite adducts with ammonium acetate in solvent-free conditions was reported in *J. of Chem. Research*, 237 (2004), however this process requires microwave irradiation. Published international application no. WO 2006/076415 describes regeneration of an aldehyde from a corresponding bisulfite adduct isolated from an alcoholic solvent system using a carbonate base with a lower alkyl carbonyl compound, for example, acetone and glyoxylic acid.

SUMMARY OF THE INVENTION

What is needed is a method using mild conditions which provides the compound of Formula I in a more purified form than has previously been available, wherein the method affords the compound in both high purity and high yield while avoiding degradation losses. These and other objectives are met by the present invention which in one aspect comprises a process for purifying the compound of Formula I

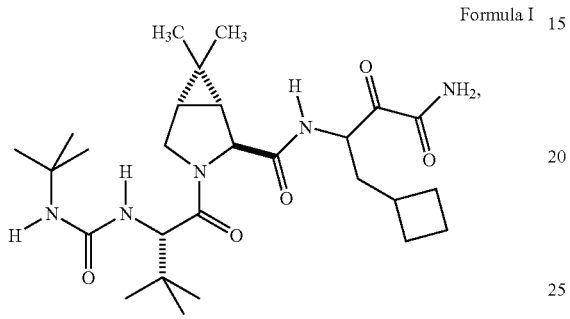

Formula I the process comprising:
  a) extracting an organic phase comprising: (i) the compound of Formula I; and (ii) one or more organic solvents, with an aqueous bisulfite solution, thereby forming an aqueous phase comprising a bisulfite adduct of the compound of Formula I; and
  b) regenerating the compound of Formula I in a precipitate form by:
    (i) a process comprising: (1) extracting the aqueous phase containing the bisulfite adduct of the compound of Formula I provided in Step "a" with an organic phase comprising one or more water-miscible organic solvents, thereby forming an organic phase containing the compound of Formula I; and (2) mixing the isolated organic phase provided in extracting Step (b)(i)(1) with water at a temperature suitable to precipitate the compound of Formula I; or
    (ii) adding the aqueous phase prepared in Step (a) into an organic phase comprising one or more water-miscible organic solvents thereby precipitating the compound of Formula I; or
    (iii) adding to the aqueous phase provided in Step (a) a carbonyl compound or an oxidant suitable to precipitate the compound of Formula I; or
    (iv) a regeneration process comprising: (1) extracting the aqueous phase provided in Step (a) with an organic phase comprising at least one organic solvent and optionally a carbonyl compound or an oxidant compound; and (2) adding the organic phase obtained in extracting step (b)(iv)(1) to a solvent or mixture of solvents in which the compound of Formula I is insoluble (an antisolvent) at a temperature suitable to precipitate the compound of Formula I.

Another aspect of the present invention comprises a process for purifying the compound of Formula I

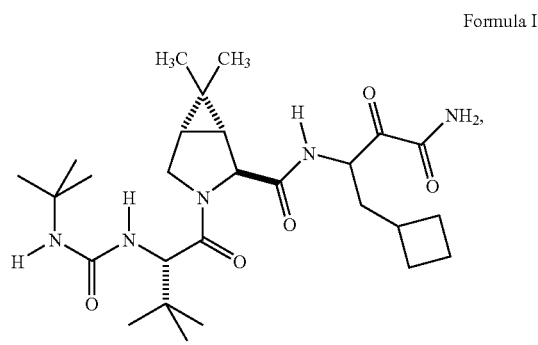

Formula I the process comprising:
  a) forming an organic phase comprising a bisulfite adduct of the compound of Formula I and one or more organic solvents;
  b) extracting the bisulfite adduct of the compound of Formula I formed in Step "a" into an aqueous phase; and
  c) regenerating the compound of Formula I in a precipitate form by:
    (i) a process comprising: (1) extracting the aqueous phase containing the bisulfite adduct of the compound of Formula I provided in Step (b) with an organic phase comprising one or more water-miscible organic solvents, thereby forming an organic phase containing the compound of Formula I; and (2) mixing the isolated organic phase provided in extracting Step (1) with water at a temperature suitable to precipitate the compound of Formula I; or
    (ii) adding the aqueous phase prepared in Step (b) into an organic phase comprising one or more water-miscible organic solvents thereby precipitating the compound of Formula I; or
    (iii) adding to the aqueous phase provided in Step (b) a carbonyl compound or an oxidant suitable to precipitate the compound of Formula I; or
    (iv) a regeneration process comprising: (1) extracting the aqueous phase provided in Step (b) with an organic phase comprising at least one organic solvent and optionally a carbonyl compound or an oxidant compound; and (2) adding the organic phase obtained in extracting step (c)(iv)(1) to a solvent or mixture of solvents in which the compound of Formula I is insoluble (an antisolvent) at a temperature suitable to precipitate the compound of Formula I.

Another aspect of the invention provides also a process for purifying a compound comprising a keto-amide, a ketone or an aldehyde, the process comprising:
  a) extracting an organic phase comprising: (i) a carbonyl compound to be purified selected from a keto-amide, a ketone; and an aldehyde; and (ii) an organic solvent or mixture of organic solvents, with an aqueous bisulfite solution, thereby forming an aqueous phase comprising a bisulfite adduct of the carbonyl compound to be purified which was initially contained in said organic phase; and
  b) regenerating the carbonyl compound to be purified by
    (i) a process comprising: (1) extracting the aqueous phase containing the bisulfite adduct of the carbonyl compound to be purified provided in Step "a" with an organic phase comprising one or more water-miscible organic solvents, thereby forming an organic phase containing the carbonyl compound to be purified; and (2) mixing the isolated organic phase provided in extracting Step "1" with water at a temperature suitable to precipitate the carbonyl compound to be purified; or (ii) adding the aqueous phase prepared in Step (a) into an organic phase comprising one or more water-miscible organic solvents thereby precipitating the carbonyl compound to be purified; or (iii) adding to the aqueous phase provided in Step (a) a carbonyl compound or an oxidant suitable to precipitate the carbonyl compound to be purified; or (iv) a regeneration process comprising: (1) extracting the aqueous phase provided in Step (a) with an organic phase comprising at least one organic solvent and optionally a carbonyl compound or an oxidant compound; and (2) adding the organic phase obtained in extracting step (b)(iv)(1) to a solvent or mixture of solvents in which the carbonyl compound to be purified is insoluble (an antisolvent) at a temperature suitable to precipitate the carbonyl compound to be purified.

Another aspect of the invention provides also a process for purifying a carbonyl compound comprising a keto-amide, a ketone or an aldehyde, the process comprising:

a) forming in an organic phase comprising: (i) an organic solvent or mixture of organic solvents; and (ii) a bisulfite adduct of a keto-amide, ketone or aldehyde compound to be purified;

b) extracting the bisulfite adduct from Step "a" into water, thereby forming an aqueous phase containing a bisulfite adduct of the keto-amide, ketone, or aldehyde compound to be purified; and c) regenerating the keto-amide, ketone or aldehyde compound from which the adduct was prepared by:

(i) a process comprising: (1) extracting the aqueous phase containing the bisulfite adduct extracted in Step "b" with an organic phase comprising one or more water-miscible organic solvents, thereby forming an organic phase containing the keto-amide, ketone or aldehyde compound comprising the adduct extracted Step "b"; and (2) mixing the isolated organic phase provided in extracting Step "(c)(i)(1)" with water at a temperature suitable to precipitate the keto-amide, ketone or aldehyde compound therefrom; or (ii) adding the aqueous phase prepared in Step (b) into an organic phase comprising one or more water-miscible organic solvents thereby precipitating the keto-amide, ketone or aldehyde compound comprising the adduct extracted in Step "b"; or (iii) adding to the aqueous phase provided in Step (b), a carbonyl compound or an oxidant suitable to precipitate the keto-amide, ketone or aldehyde compound comprising the adduct extracted in Step "b"; or (iv) a regeneration process comprising: (1) extracting the aqueous phase provided in Step (b) with an organic phase comprising at least one organic solvent and optionally a carbonyl compound or an oxidant compound; and (2) adding the organic phase obtained in extracting step (c)(iv)(1) to a solvent or mixture of solvents in which the keto-amide, ketone or aldehyde compound comprising the adduct extracted in Step "b" is insoluble (an antisolvent) at a temperature suitable to precipitate said the keto-amide, ketone or aldehyde compound.

In some embodiments of the inventive process it is preferred to employ an organic phase during the bisulfite adduct formation which is selected from acetates, for example, methyl acetate, ethyl acetate and isopropyl acetate, ethers, for example methyl tertiary-butyl ether (MTBE), and hydrohalocarbons, for example, methylene chloride. In some embodiments using low polarity solvents and the process of Scheme II, it is preferred to use high concentrations of an aqueous bisulfate solution, for example, above about 10 wt % aqueous bisulfate solution and a saturated aqueous bisulfite solution. In some embodiments utilizing the process of Scheme III it is preferred to use low concentrations of a bisulfite solution, for example, below about 10 wt % aqueous bisulfite solution. In some embodiments utilizing the process of Scheme III using aqueous bisulfite solutions above about 10 wt % aqueous bisulfite solution, it is preferred to employ an aqueous phase having about the same polarity as an acetate or a mixture of acetates, preferably ethyl acetate. Other aspects of the invention will become apparent from the following description of the invention.

DETAILED DESCRIPTION OF THE INVENTION

The present process has several advantages over the reported methods. It eliminates isolation of a bisulfite adduct (i.e., eliminates a filtration step); a bisulfite adduct is obtained as a water solution, which can be directly used for regeneration of a carbonyl compound, for example, by extraction. It avoids highly acidic conditions or basic conditions. Additives such as carbonyl compounds or oxidants, which are used for regeneration, are freely soluble in water, and a regenerated product is obtained as a solution in organic solvents, which can be used for isolation of the product without removal of co-products. No special equipment such as a microwave is required.

Further, the process of the present invention minimizes degradation and dimer formation during purification. The bisulfite adduct of the compound is a protected form of an alpha-keto amide and is greatly stabilized. Because of the water solubility of the adduct, organic impurities can be removed effectively by two-phase extraction. The four different regeneration methods offer flexibility depending on the chemical and physical properties of alpha-keto amides. The method of the invention has a further significant advantage when the compound is produced by DMSO-mediated oxidation reactions such as Swern or Moffatt oxidations: the odor that results from dimethyl sulfide or other sulfur-containing by-products can be effectively removed through the bisulfite purification.

Previously published procedures for preparing the compound resulted in about 63% to about 98.5% purity; using the process of the present invention results in about 97.2% to about 99.8% purity.

Moreover, the various advantages provided by the process of the invention make the process particularly suitable for scale up to provide pure compound in large quantities, thus, the process of the invention is suitable for large-scale purifications.

In one aspect the process of the invention is shown schematically in Scheme II, below. In step one of Scheme II, an organic phase comprising the compound of Formula I is treated with an aqueous phase comprising bisulfite, thereby forming an aqueous solution of the bisulfite adduct of the compound of Formula I, which is subsequently regenerated from the aqueous phase without isolating the bisulfite adduct. In this aspect of the process, it is preferred to employ as the organic phase, very non-polar solvents, for example, but not limited to, ethers, for example, but not limited to, methyl tertiarybutyl ether (MTBE). When an organic phase which is more polar is employed, for example, ethyl acetate, it is preferred to employ an aqueous phase which is less than about 10 wt. % concentration in bisulfite to insure that the bisulfite adduct is taken up in the aqueous phase. It will be appreciated that for the process of Scheme II, organic phases of different polarity can be used by adjusting the concentration of bisulfite used in the aqueous phase.

SCHEME II

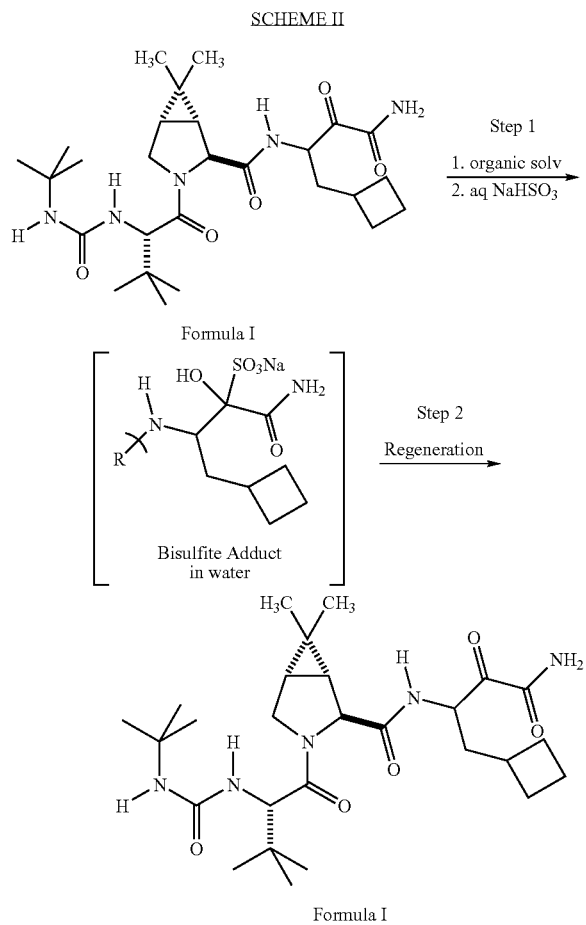

Formula I wherein

refers to the rest of the molecule, i.e.,

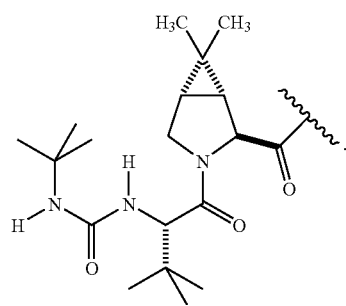

In Step 1 of the process shown in Scheme II, a solution of the compound of Formula I in an organic solvent or mixture of organic solvents comprises an organic phase which is extracted with a dilute aqueous bisulfite solution to obtain, in the aqueous phase, a bisulfite adduct of the compound of Formula I (hereinafter, the adduct). Preferably, the aqueous phase comprises less than about 10% of bisulfite, more preferably the aqueous phase comprises about 1% to about 3% bisulfite. In some embodiments it is preferred to prepare the aqueous phase from a bisulfite source selected from sodium bisulfite, sodium metabisulfite, potassium metabisulfite and other similar bisulfites, more preferably sodium bisulfite is employed. It will be appreciated that suitable organic solvents for use in preparing an organic phase comprising the compound of Formula I for use in Step 1 of the process shown in Scheme II can include any very low polarity solvent having about the same, or lower polarity than MTBE, and mixtures of organic solvents having low polarity. As mentioned above, solvents of higher polarity can be employed with appropriate adjustment in the concentration of bisulfite in the aqueous phase. Accordingly, acetates, for example, ethyl acetate, and other solvents or solvent mixtures having about the same polarity can be employed as the organic phase when the concentration of bisulfite in the aqueous phase is less than about 10 wt %.

In some embodiments of the process of Scheme II, it is preferred to carry out step 1 (extraction and formation of the bisulfite adduct) at a temperature ranging from about −5° C. to about 10° C., preferably from about 3° C. to about 4° C. Without ascribing to theory, in general, at higher temperature, a lower extraction yield is obtained. Multiple extractions (2 to 5, preferably 2 to 3) may be performed to increase the yield of bisulfite adduct obtained.

In some embodiments in which the purified compound is precipitated from an aqueous phase, it is preferred to concentrate the aqueous phase provided from Step 1 by distilling the aqueous phase under vacuum at a temperature below 25° C. to remove organic volatiles (volatiles stripping), which are present in the aqueous phase. When a volatiles stripping step is carried out, the removal of the volatiles from the aqueous phase from which the carbonyl compound to be purified is precipitated thereby improves the physical properties of the regenerated precipitated, that is to say, prevents the formation of a gummy precipitate. In some embodiments utilizing volatiles stripping it is preferred to add a small amount of bisulfite aqueous solution, preferably aqueous sodium bisulfite, to the separated aqueous phase to stabilize the adduct as well as to reduce foam formation during distillation.

Step 2 of Scheme II shows regeneration of the compound of Formula I from the bisulfite adduct comprising the aqueous phase, Regeneration of the purified compound from the adduct in aqueous solution is accomplished using one of four regeneration methods:

a) extracting the aqueous phase containing the bisulfite adduct of the compound of Formula I with an organic phase comprising one or more water-miscible organic solvents followed by precipitating the compound of Formula I from the organic phase by mixing the organic phase containing the compound of Formula I with water;

b) directly precipitating the compound of Formula I from the aqueous phase containing a bisulfite adduct of the compound of Formula I by mixing the aqueous phase with at least one water-miscible organic solvent;

c) precipitating the compound of Formula I by contacting the aqueous phase containing a bisulfite adduct of the compound of Formula I with: (i) a carbonyl compound; or (ii) an oxidant; and d) a regeneration process comprising: (1) extracting the aqueous phase comprising a bisulfite adduct of the compound of Formula I with an organic phase comprising at least one organic solvent and optionally a carbonyl compound or an oxidant compound; and (2) mixing the organic phase obtained in extracting step "d1" with a solvent or mixture of solvents in which the compound of Formula I is insoluble (an antisolvent), wherein the temperature of the mixture is suitable to precipitate the compound of Formula I.

Each of these regeneration methods are discussed next.

Regeneration Option (a): extraction of the compound of Formula I from the aqueous phase containing the bisulfite adduct into water-miscible organic solvents followed by precipitation with an antisolvent.

In this optional method of regenerating the compound of Formula I, the aqueous phase comprising a bisulfite adduct of the compound of Formula I obtained in Step 1 is contacted with an organic phase comprising at least one water-miscible organic solvent, optionally the organic phase comprises a mixture of more than one water-miscible organic solvent, optionally in the presence of an inorganic salt of suitable concentration to maintain phase separation, to produce a solution of the compound of Formula I in the organic phase. Examples of suitable water-miscible solvents include, but are not limited to, acetone, tetrahydrofuran, acetonitrile and mixtures thereof. In some embodiments acetone is preferred as the water-miscible solvent.

Optionally, inorganic salts are used to improve phase separation. When employed, examples of suitable inorganic salts include, but are not limited to, sodium chloride, lithium chloride, potassium chloride, sodium bromide and the like, with sodium chloride being preferred. In some embodiments employing inorganic salts it is preferred to employ a saturated salt solution. In some embodiments it is preferred to carry out the extraction with the mixed phases maintained at temperature of from about 15° C. to about 30° C. Thus obtained, the resulting organic phase containing the compound of Formula I can optionally be washed further with an inorganic salt solution (preferably a sodium chloride solution) to reduce residual bisulfite content. In some embodiments, once obtained, it is preferred to add the organic phase containing the compound of Formula I to water at a temperature of from about 15° C. to about 30° C. to precipitate out the compound of Formula I. In some embodiments it is preferred to isolate the precipitate by filtration and optionally the wet cake is dried under vacuum to obtain the purified compound as a white solid.

Regeneration Option (b): direct precipitation of the compound of Formula I from an aqueous phase comprising a bisulfite adduct of the compound of Formula I by contacting the aqueous phase with one or more water-miscible solvents.

In this optional method of regenerating the compound of Formula I, the aqueous phase comprising a bisulfite adduct of the compound of Formula I obtained in Step 1 is admixed with at least one water-miscible solvent and water or to a mixture of water-miscible solvents and water, thereby forming a precipitate comprising the compound of Formula I. The precipitate is isolated by filtration and the wet cake is dried under vacuum to obtain the purified compound as a white solid. Examples of suitable water-miscible solvents include, but are not limited to, acetone, tetrahydrofuran, acetonitrile and mixtures thereof, with the preferred water-miscible solvent being acetone. Use of acetone is superior to other solvents since acetone can trap bisulfite as an acetone-bisulfite adduct.

Regeneration Option (c): direct precipitation by contacting with a carbonyl compound or an oxidant.

In this optional method of regenerating the compound of Formula I, the aqueous phase comprising a bisulfite adduct of the compound of Formula I obtained in Step 1 is contacted with a water-soluble carbonyl compound or an oxidant, thereby precipitating the compound of Formula I. In some embodiments it is preferred to maintain the mixture of aqueous phase comprising a bisulfite adduct of the compound of Formula I at a temperature of from about 0° C. to about 30° C. In some embodiments it is preferred to obtain the resulting precipitate by filtration followed by washing and drying the collected solids under vacuum to give the purified compound of Formula I as a white solid.

Examples of suitable carbonyl compounds include, but are not limited to, glyoxal, glyoxylic acid or a salt thereof, pyruvic acid or a salt thereof, and ketones, for example, acetone. In some embodiments using a carbonyl compound, it is preferred to use glyoxal, glyoxylic acid and sodium glyoxylate. Examples of suitable oxidants include, but are not limited to, oxone, potassium persulfate, ammonium persulfate, and sodium persulfate. In some embodiments employing an oxidant, it is preferred to use sodium persulfate. In some embodiments employing a carbonyl compound or an oxidant, it is preferred to use from about 0.5 to about 2.0 equivalents relative to the amount of the compound of Formula I to be precipitated, preferably about 1 equivalent is used.

Regeneration Option (d): extraction into a phase comprising an organic solvent or mixture of organic solvents, optionally in the presence of a carbonyl compound or an oxidant, followed by adding the organic phase extract into a solvent or mixture of solvents in which the compound of Formula I is insoluble.

In this optional method of regenerating the compound of Formula I, the aqueous phase comprising a bisulfite adduct of the compound of Formula I obtained in Step 1 is extracted with an organic phase comprising an organic solvent or mixture of organic solvents. In some embodiments it is preferred to carry out this extraction at a temperature of from about 0° C. to about 50° C. The resultant organic phase contains the compound of Formula I and optionally is washed with water to remove residual water-soluble impurities. Thus obtained, the organic phase is contacted with a solvent or mixture of solvents in which the compound of Formula I is insoluble (an anti-solvent). In some embodiments it is preferred to carry out the second step of this optional method of regenerating the compound of Formula I at a temperature of from about −30 to about +30° C., thereby precipitating the compound. Thus obtained, optionally the precipitate is obtained by filtration, and the filter cake is optionally washed with one or more aliquots of anti-solvent(s) and dried under vacuum to give the purified compound as a white solid. Optionally, the slurry of the product is concentrated by distillation before filtration, thereby removing or reducing the concentration of organic solvents in order to improve the physical property of the precipitate. Examples of suitable organic solvents for use in this optional method of regeneration include, but are not limited to, ethyl acetate, methylene chloride, isopropyl acetate, methyl acetate, tertiarybutyl methyl ether (MTBE) and mixtures thereof. In some embodiments it is preferred to employ MTBE as the organic phase. Examples of suitable anti-solvents for use in this optional method of regeneration include, but are not limited to, pentane(s), hexane(s), heptane(s), cyclohexane, octane and mixtures thereof. In some embodiments it is preferred to use heptane(s) as an antisolvent. Optionally, inorganic salts, for example, sodium chloride, lithium chloride, potassium chloride, and sodium bromide can be added during the extraction step to improve the yield of the compound of Formula I extracted.

Optionally, the extraction step is carried out in the presence of a carbonyl compound or an oxidant to facilitate regeneration of the compound. Examples of suitable carbonyl compounds which can be optionally employed include, but are not limited to, glyoxal, glyoxylic acid or a salt thereof, pyruvic acid or a salt thereof, and ketones, for example, acetone. Examples of suitable oxidants which can be optionally employed include, but are not limited to, oxone, potassium persulfate, and sodium persulfate. 1-1.5 equivalents of the oxidant or carbonyl compound are used, with more than 1 equivalent being preferred.

In some embodiments of the invention, the process is carried out in accordance with the process shown schematically in Scheme III, wherein a bisulfite adduct of the compound of Formula I is prepared in an organic phase, the adduct is extracted into an aqueous phase in Step B, and then in Step C of Scheme III, the compound of Formula I is regenerated from the aqueous phase provided in Step B using one of the four optional regeneration processes (A to D) described above for the process of Scheme II in Step 2. When the process of Scheme III is employed, it is preferred to use an organic phase comprising polar organic solvents, for example, but not limited to, acetates, for example, ethyl acetate.

SCHEME III

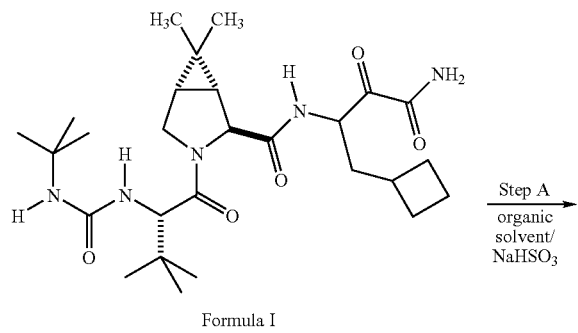

Formula I

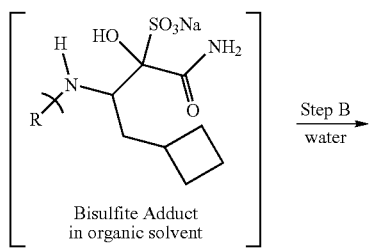

Bisulfite Adduct in organic solvent

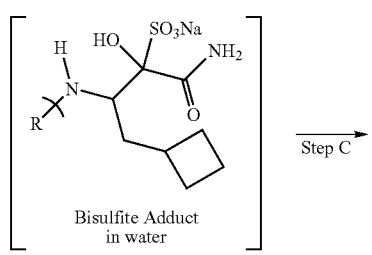

Bisulfite Adduct in water

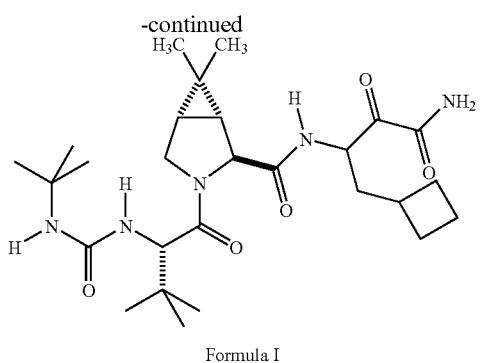

Formula I

In accordance with the process presented schematically in Scheme III, Step A comprises contacting an organic phase comprising at least one organic solvent and the compound of Formula I with a bisulfite source to provide a bisulfite adduct of the compound of Formula I in the organic phase. In some embodiments it is preferred to mix the organic phase with an aqueous phase comprising bisulfite as a means of contacting the organic phase with a source of bisulfite. In some embodiments it is preferred to employ high polarity solvents or mixtures of solvents, for example, acetates, and mixtures having similar polarity, as the organic phase. In some embodiments it is preferred to employ concentrations of bisulfite in the aqueous phase which are above at least about 10 wt. % bisulfite. It will be appreciated that in keeping with the present invention, an organic phase of lesser polarity than acetate can be employed in the process of Scheme III by adjusting the concentration of bisulfite in the aqueous phase. In some embodiments employing an aqueous phase comprising bisulfite it is preferred to employ an aqueous solution which contains from about 10 wt. % bisulfite to a sufficient amount of bisulfite to form a saturated bisulfite solution. For the process of Scheme III, suitable sources of bisulfite include, but are not limited to, sodium bisulfite, sodium metabisulfite, and potassium metabisulfite. In some embodiments it is preferred to use sodium bisulfite to prepare an aqueous phase. Examples of organic solvents suitable for use as the organic phase in Step A of the process shown in Scheme III include, but are not limited to, halohydrocarbons, for example, methylene chloride, acetates, for example, but not limited to, ethyl acetate, isopropyl acetate, and methyl acetate, and mixtures thereof. It will be appreciated that the organic phase can comprise any organic solvent or mixture of organic solvents providing an organic phase having about the same polarity as acetates in which the adduct of the compound to be purified by the process shown in Scheme III, for example, the compound of Formula I, is soluble, and with appropriate adjustment to the concentration of bisulfite in the aqueous phase to insure that the bisulfite adduct is taken up in the organic phase. In some embodiments it is preferred to employ ethyl acetate, alone or admixed with MTBE, as the organic phase. In some embodiments it is preferred to carry out Step A, formation of a bisulfite adduct of the compound of Formula I, at a temperature of from about 10° C. to about 30° C., preferably at a temperature of from about 20° C. to about 30° C.

In Step B of Scheme III, the organic phase containing a bisulfite adduct of the compound of Formula I is extracted with cold water. In some embodiments, it is preferred for the extraction step to be accompanied by agitation of the mixed phases. It will be appreciated that with a shorter agitation time a higher yield of the compound of Formula I is provided subsequent in Step C. In some embodiments employing agitation, it is preferred to agitate the mixed phase for a period of from about 2 minutes to about 10 minutes, more preferably about 5 minutes of agitation are used.

In some embodiments it is preferred for the extraction to be carried out at a temperature ranging from about −5° C. to about 30° C. It will be appreciated that when higher temperatures are employed in Extraction Step (B), increasing amounts of the compound of Formula I are regenerated from the bisulfite adduct present in the organic phase, and accordingly, increasing amounts of the compound of Formula I will be retained in the organic layer, resulting in a lower yield of purified compound of Formula I when it is regenerated from the aqueous extract in Step C of Scheme III. In some processes it is preferred to separate the organic phase at the end of Extraction Step B and repeat steps "A" and "B" to increase the amount of the bisulfite adduct extracted from the organic phase.

In some embodiments it is preferred to employ a dilute aqueous bisulfite solution in place of water as the aqueous phase. In some embodiments employing a bisulfite solution as the aqueous phase in Extraction Step "B" it is preferred to employ an aqueous solution comprising less than about 3 wt. % of bisulfite.

As with the aqueous phase comprising the bisulfite adduct of the compound of Formula I provided in Step 1 of Scheme II, above, optionally, in embodiments in which the purified compound comprising the adduct is precipitated directly from the aqueous phase in which the bisulfite adduct is taken up in the process of Scheme III, it is preferred to concentrate the aqueous phase provided in Step B of Scheme III (comprising a bisulfite adduct of Formula I) under vacuum at a temperature below 25° C. to remove residual organic volatiles (volatiles stripping) to improve the properties of the precipitated product, that is to say, avoids the formation of a "gummy" precipitate. In some embodiments of the process of Scheme III employing a volatiles stripping step prior to regeneration Step "C", prior to stripping volatiles a small amount of bisulfite aqueous solution, preferably sodium bisulfite, is added to stabilize the adduct as well as to reduce foam formation during distillation.

Once the aqueous phase provided in Step B of Scheme III is separated, the purified compound of Formula I can be regenerated and precipitated by utilizing any of Regeneration Options A to D described above for Regeneration Step 2 of the process of Scheme II.

In an alternative procedure for the process of Scheme III, above, once bisulfite adduct formation Step A is completed, the organic phase comprising the bisulfite adduct of the compound of Formula I can optionally be subjected to a solvent swap, replacing the organic solvent in which the bisulfite adduct was prepared with an organic solvent suitable for carrying out the process of Scheme II. Once the organic solvent in the organic phase has been replaced in accordance with this optional procedure, the phase is concentrated under vacuum, and a water-miscible solvent as defined above is added. The mixture thus provided is added to water to precipitate out the purified compound of Formula I in accordance with Scheme II, Step ii, Regeneration Option A described above for the process of Scheme II.

The bisulfite purification process of the invention can be carried out utilizing either the isolated solid compound of Formula I or a solution containing the compound of Formula I prepared in accordance with a synthetic procedure for preparing the compound of Formula I, for example, the procedure disclosed in U.S. Pat. No. 7,012,066 (the '066 patent), which is incorporated herein by reference. One example of such a procedure is Example XXIV of the '066 patent, which discloses a typical procedure for providing the compound of Formula I as a solution in detail. Additional examples of suitable procedures for the provision of the compound of Formula I either as an isolated solid or as a solution can be found in Published U.S. Patent Application No. US2005/0249702 (the '9702 publication), which is incorporated herein by reference. The '9702 publication discloses preparation of the compound of Formula I and its separation into diastereomers.

Published U.S. patent application no. 2007/0149459, published Jun. 28, 2007, discloses several alternate procedures for oxidizing the intermediate compound of the Formula II:

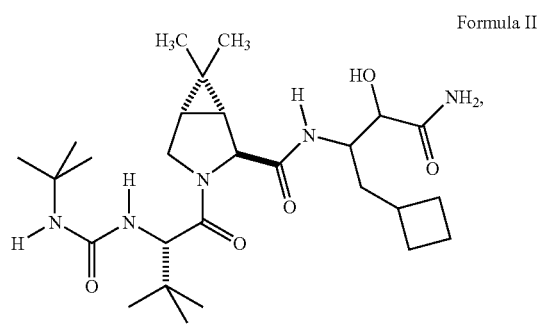

Formula II to obtain the compound of Formula I.

In some embodiments it is preferred to use the process of Scheme II to prepare a bisulfite adduct. In some embodiments of the process of Scheme II it is preferred to use sodium bisulfite as the bisulfite source and methyl tertiarybutylether (MTBE) as the organic phase solvent. In some embodiments it is preferred to carry out the extraction Step 2 (Scheme II) at a temperature of from about −5° C. to about 10° C. In some embodiments of the invention employing the process of Scheme II it is preferred to employ optional regeneration method "d" in Step 2 of Scheme II. In some embodiments utilizing optional regeneration method "d" in Step 2 of Scheme II it is preferred to utilize MTBE and the organic phase used for extraction. In some embodiments employing optional regeneration process "d" wherein an optional carbonyl compound or an oxidizer is employed in Step (d)(1) of the regeneration process, it is preferred when selecting a carbonyl compound, to employ a glyoxylic acid salt.

In some embodiments it is preferred to use the process of Scheme III. In some embodiments utilizing the process of Scheme III it is preferred to employ sodium bisulfite as the bisulfite source. In some embodiments utilizing the process of Scheme III it is preferred to utilize an organic solvent selected from ethyl acetate, ethyl acetate/MTBE mixtures as the organic phase. In some embodiments utilizing the process of Scheme III it is preferred to carry out Step 2 (extraction) with the phases maintained at a temperature of from about −5° C. to about 10° C. In some embodiments utilizing the process of Scheme III it is preferred to utilize as a regeneration process in Step "C" the optional regeneration process described as option "d" in Step "2" of the process of Scheme II, above. In some embodiments using the process of Scheme III and optional regeneration process "d" it is preferred to utilize MTBE as the organic solvent in the regeneration process. In some process utilizing optional regeneration process "d" and a carbonyl compound in Step (d)(1), it is preferred to employ a glyoxylic acid salt as the carbonyl compound.

It will be appreciated that by selecting appropriate reagents and reaction conditions consistent with the teachings of the present specification, the process of the present invention is suitable for providing purification to a wide range of carbonyl compounds selected from keto-amide, ketone and aldehyde compounds using either the process of Scheme II or Scheme III. Purification of such compounds can be accomplished by carrying out the processes described herein making adjustments in the solvents used in the process, if necessary, to account for different solubilities of the compound to be purified.

There follows examples which illustrate the processes of the invention. In the following examples of typical procedures, the following abbreviations are used: EtOAc (ethyl acetate); Et$_3$N (triethylamine); DMSO (dimethyl sulfoxide); and EDCl (1-dimethylaminopropyl-3-ethylcarbodiimide).

EXAMPLE 1

Purification Process of Scheme III, Regeneration Option "a"

Preparation of Compound: To a reactor was charged (16.5 kg) of the compound of Formula II,

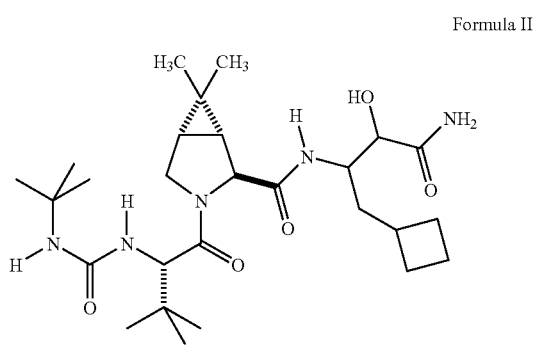

Formula II 24.3 Kg of EDCl, and 190 L of EtOAc. The batch temperature was adjusted between 15 and 25° C. At the same temperature, Et$_3$N (9.60 kg, 3 eq) followed by EtOAc rinse (8 L) was charged. To the resultant mixture was charged DMSO (83 L) while maintaining the temperature of the batch between 15° C. and 25° C. CH$_3$SO$_3$H (10.89 kg) was charged while maintaining the reaction mixture between 15° C. and 30° C. After agitating at the reaction mixture for 1.5 hours while maintaining the reaction mixture between 20° C. and 30° C., the reaction mixture was cooled to a temperature between −5° C. and 5° C.

Purification of the Compound of Formula I

In a separate reactor was charged 165 L of water and 33 L of EtOAc, and the mixture was cooled below 5° C. The reaction mixture containing the compound was transferred into the mixture of cold water/EtOAc at 0 to 10° C. The organic layer was separated and washed with water (99 L) three times.

Step 1: To the resulting organic solution was added NaHSO$_3$ aqueous solution (prepared from 49.5 kg of NaHSO$_3$ and 109 L of water). The whole was agitated for 3 h at 20-30° C. The aqueous NaHSO$_3$ layer was separated and saved. The organic layer was concentrated to about 116 L of volume and diluted with MTBE (220 L). The separated aqueous NaHSO$_3$ layer was added to the organic layer. The resultant mixture was agitated for 3 h at 20-30° C. The organic layer was separated and cooled to 0-10° C.

Step 2: To the cooled organic layer of Step 1 was added cold water (165 L, 0-10° C.) without agitation, and the whole was agitated for 5 min. The aqueous layer was separated, and a solution of water (2 L) containing NaHSO$_3$ (0.71 kg) was added to the water layer. The water layer was distilled to the final volume of about 171 L under vacuum below 25° C. to remove volatiles.

Step 3: (Regeneration method a): The resultant water layer of Step 2 was added into a slurry of NaCl (49.5 kg) in acetone (83 L) at 20-30° C. The separated acetone layer followed by acetone rinse (8 L) was added through a 0.2 micron filter to water (347 L) over 20 min at 15-25° C. After agitation for about 1 h, the precipitate was filtered and washed with water (83 L). The wet cake was dried under vacuum at 30-40° C. to produce 13.0 kg (79%) of the purified compound as a white solid.

EXAMPLE 2

Purification Process of Scheme III, Regeneration Option "b"

Preparation of Compound: To a reactor were charged the compound of Formula II (17.5 kg), 25.7 kg of EDCl, and 202 L of EtOAc. The batch temperature was adjusted between 15 and 25° C. At the same temperature, Et$_3$N (10.2 kg, 3 eq) followed by EtOAc rinse (9 L) was charged. To the resultant mixture was charged DMSO (88 L) while maintaining the temperature at 15 to 25° C. CH$_3$SO$_3$H (11.6 kg) was charged at 15 to 30° C. After agitating at 20-30° C. for 1.5 h, the reaction mixture was cooled to −5 to 5° C. To another reactor were charged water (175 L) and EtOAc (35 L) and the mixture was cooled below 5° C. The reaction mixture containing the compound was transferred into the mixture of cold water/EtOAc at 0 to 10° C. The organic layer was separated and washed with water (105 L) three times.

Purification of the Compound of Formula I

Step 1: To the resulting organic solution was added NaHSO$_3$ aqueous solution (prepared from 52.5 kg of NaHSO$_3$ and 116 L of water). The whole was agitated for 3 hours while maintaining the reaction mixture at a temperature between 20° C. and 30° C. The aqueous NaHSO$_3$ layer was separated and saved. The organic layer was concentrated to about 140 L of volume and diluted with MTBE (233 L). The separated aqueous NaHSO$_3$ layer was added to the organic layer. The resultant mixture was agitated for 3 h at 20-30° C. The organic layer was separated and cooled to 0-10° C.

Step 2: To the cooled organic layer from Step 1 was added cold water (175 L, 0-6° C.) without agitation, and the whole was agitated for 5 min. The aqueous layer was separated, and a solution of water (2 L) containing NaHSO$_3$ (0.8 kg) to the water layer was added. The water layer was distilled to the final volume of about 190 L under vacuum below 25° C. to remove volatiles.

Step 3: The resultant water layer from Step 2 was added through a 0.2 micron filter to a mixture of water (193 L) and acetone (53 L) at 15-25° C. After agitation for about 4 h, the precipitate was filtered and washed with water (263 L). The wet cake was dried under vacuum at 30-40° C. to produce 11.4 kg (65%) of the purified compound as a white solid.

EXAMPLE 2A

Purification Process Scheme III, Regeneration Option "b"

Step 1: The compound of Formula I (5.9 kg, 87.3% purity) was dissolved in EtOAc (39 L) and MTBE (79 L). To the resulting organic solution was added NaHSO$_3$ aqueous solution (prepared from 17.7 kg of NaHSO$_3$ and 39 L of water). The whole was agitated for 1 h at 15-25° C. The aqueous NaHSO$_3$ layer, which is used later, was separated. The organic layer was cooled to 0-10° C.

Step 2: To the cooled organic layer from Step 1 was added cold water (59 L at 0-10° C.) without agitation, and the whole was agitated for 5 min. To the separated water layer was added a solution of water (1 L) containing NaHSO$_3$ (0.3 kg). The water layer was distilled to the final volume of about 72 L under vacuum below 25° C. to remove volatiles.

Step 3: The resultant water layer from Step 2 was added through 0.2 micron filter to a mixture of water (65 L) and acetone (18 L) at 15-25° C. After agitation for about 4 h, the precipitate was filtered and washed with water (89 L). The wet cake was dried under vacuum at 30-40° C. to produce 3.0 kg (53, 98.3% purity) of the purified compound as a white solid.

EXAMPLE 3

Purification Process Scheme III, Regeneration Option "c"

Step 1: The compound of Formula I (31.1 g) was dissolved in EtOAc (200 mL) and MTBE (400 mL). 40% NaHSO$_3$ aqueous solution (225 mL) was added. The resultant two-phase mixture was agitated at room temperature for 3 h. The organic layer was separated and cooled to 3° C.

Step 2: Cold water cooled to 3.5° C. (300 mL) was added to the product of Step 1 and the mixture was agitated for 3 min. The separated water layer was concentrated at 25° C. (jacket temperature) under vacuum starting at 160 mmHg and finally at 55 mmHg for 2.5 h.

Step 3: The resultant water solution from Step 2 was cooled to 8° C., and 40% glyoxal in water (9.9 mL) was added over 30 min. The resultant slurry was agitated at 8° C. for 30 min and was allowed to reach at 25° C. After additional agitation for 3 h at 25° C., the precipitate was filtered, washed with water (300 mL), and dried under vacuum at 30-40° C. The purified compound (20.7 g, 67%) was obtained as a white solid.

EXAMPLE 3A

Purification Process of Scheme III, Regeneration Option "c", with Carbonyl Compound Present A solution of adduct in water (prepared as above in Example 3, steps 1 and 2, 45.2 g containing 4.15 g of the compound) was cooled to 8° C., and 50% glyoxylic acid in water (5.8 mL) was added. The resultant slurry was agitated at 8° C. for 1 h and was allowed to reach at 25° C. After additional agitation for 3 h at 25° C., the precipitate was filtered, washed with water, and dried under vacuum at 50° C. The purified compound (2.71 g, 65%) was obtained as a white solid.

EXAMPLE 3B

A solution of adduct in water (prepared as above in Example 3A, 45.2 g containing 4.15 g of the compound) was cooled to 8° C., and sodium glyoxylate solution (prepared from 3 equiv each of 50% glyoxylic acid in water and 25% NaOH) was added over 20 min. The resultant slurry was agitated at 8° C. for 1 h and was allowed to reach at 25° C. After additional agitation for 3 h at 25° C., the precipitate was filtered, washed with water, and dried under vacuum at 50° C. The purified compound (2.14 g, 52%) was obtained as a white solid.

EXAMPLE 4

Purification Process Scheme III, Regeneration Option "d"

Preparation of Compound: To a reactor were charged the compound of Formula II (18.0 kg), EDCl (26.5 kg), and EtOAc (81 L). The batch temperature was adjusted between 15 and 25° C. At the same temperature, Et$_3$N (7.8 kg) followed by EtOAc rinse (9 L) was charged. To the resultant mixture was charged DMSO (36 L) while maintaining the temperature at 15 to 25° C. CH$_3$SO$_3$H (8.9 kg) was charged at 15 to 32° C. After agitating at 20-30° C. for 1.5 h, the reaction mixture was cooled to −5 to 5° C. To another reactor were charged water (90 L) and EtOAc (18 L) and the mixture was cooled below 10° C. The reaction mixture containing the compound was transferred into the mixture of cold water/EtOAc at 0 to 10° C. The water layer was separated and extracted with EtOAc (72 L). The combined organic layers were washed with water (90 L) three times, and its volume was adjusted to 216 L by addition of 30 L of EtOAc. HPLC assay of the EtOAc solution showed 88.7% purity of the compound of Formula I.

Purification of the Compound of Formula I

Step 1: To the resulting organic solution was added NaHSO$_3$ aqueous solution (prepared from 28.8 kg of NaHSO$_3$ and 63 L of water). The whole was agitated for 1 h at 15-25° C. The aqueous NaHSO$_3$ layer was separated. The organic layer was cooled to −7 to 1° C.

Step 2: To the cooled organic layer was added cold water (270 L 1-7° C.) with agitation, and the agitation was stopped after finishing the cold water charge.

Step 3: The cold water layer was separated and MTBE (90 L) was added at −2 to 8° C. The two-phasic mixture was heated to 15-25° C., and the sodium glyoxylate solution was added at the same temperature. After 1 h agitation, the organic layer was separated and washed with water (90 L). The organic layer was cooled to −5 to 5° C. and was added to cold heptane (702 L) at −25 to −15° C. over about 30 min. The resultant slurry was concentrated to about 530 L. The precipitate was filtered and washed with heptane (54 L). The wet cake was dried under vacuum to produce 10.6 kg (61%) of the purified compound as a white solid. HPLC assay showed 99.8% purity of the isolated compound of Formula I.

EXAMPLE 5

Purification Process of Scheme II, No Regeneration Step

Step 1: The compound of Formula I (10 g, 86% purity) was dissolved in MTBE (120 mL). 1.3% NaHSO$_3$ aqueous solution (prepared from 2.0 g of NaHSO$_3$ and 150 mL water) was added, and the whole was cooled to about 3° C. and agitated for 1 h. The water layer was separated at the same temperature. HPLC analysis showed 5.93 g (59%, 99.0% purity) of the purified compound in the water layer.

EXAMPLE 5A

Purification Process of Scheme II, No Regeneration Step

Step 1: The compound of Formula I (10 g, 86% purity) was dissolved in MTBE (120 mL). 1.3% NaHSO$_3$ aqueous solution was prepared from 2.0 g of NaHSO$_3$ and 150 mL water. 100 mL of the bisulfite solution was added to the solution of the compound in MTBE. The whole was cooled to about 4° C. and agitated for 1 h. The water layer was separated at the same temperature. HPLC analysis showed 5.74 g (57%, 98.2% purity) of the compound in the water layer. To the organic layer was added about 50 mL of the bisulfite solution prepared above, and whole was cooled to about 4° C. and agitated for 1 h. HPLC analysis of the separated water layer showed 1.26 g (13%, 99.6% purity) of the compound. Total 7.00 g (70%) of the purified compound was obtained by two extractions.

EXAMPLE 6

Purification Process of Scheme III, Regeneration Option "d"

Step 1: The compound of Formula I (20.0 g) was dissolved in EtOAc (240 mL). 40% NaHSO$_3$ aqueous solution (prepared from 32 g of NaHSO$_3$ and 70 mL of water) was added. The resultant two-phasic mixture was agitated at room temperature overnight. The organic layer was separated and cooled to 3° C.
Step 2: Cold water cooled to 3° C. (000 mL) was added to the product of Step 1 and the whole was agitated for 10 min.
Step 3: To the separated water layer from Step 2 containing the adduct was added MTBE (100 mL), and the resultant mixture was warmed to 30° C. and agitated for 30 min at the same temperature. The MTBE layer was separated, and to the water layer was added MTBE (100 mL). The resultant mixture was agitated for 30 min at 30° C. The MTBE layer was separated. The combined MTBE layers were washed with water (100 mL). HPLC assay showed 10.4 g (52%) of the purified compound in the MTBE extracts.

EXAMPLE 6A

Purification Process of Scheme III, Regeneration Option "d"

To a solution of the bisulfite adduct of the compound of Formula I in water (124.0 g containing 8.9 g of the compound) were added MTBE (100 mL) and saturated NaCl solution (30 mL). The resultant mixture was warmed to 30° C. and agitated for 30 min at the same temperature. The MTBE-layer was separated and washed with water (50 mL). HPLC assay showed 7.46 g (84%) of the purified compound in the MTBE extract.

EXAMPLE 6B

To a solution of the adduct in water (prepared as above, 121.7 g containing 8.45 g of the compound) was added MTBE (100 mL) followed by a suspension of potassium persulfate (10.4 g) in water (20 mL) at 25° C. After 45 min agitation at 25° C., the MTBE layer was separated and washed with water (50 mL). HPLC assay showed 7.41 g (88%) of the purified compound in the MTBE extract.

EXAMPLE 6C

To a solution of the adduct in water (prepared as above, 127.0 g containing 8.82 g of the compound) was added MTBE (100 mL) followed by a suspension of oxone (11.8 g) in water (40 mL) below 25° C. After 1 h agitation at 25° C., the MTBE layer was separated and washed with water (50 mL). HPLC assay showed 8.30 g (94%) of the purified compound in the MTBE extract.

HPLC Determination of Purity

The purity of the compound of Formula I is determined by HPLC according to the methods described below:

| Column | YMC Pack Pro-C18, 4.6 mm × 150 mm, 3-µm | | |
|---|---|---|---|
| Solvent | Solvent A: Methanol: 20 mM phosphate buffer, pH 7.0 (10:90, v:v) Solvent B: Methanol: 20 mM phosphate buffer, pH 7.0 (90:10, v:v) | | |
| | Time (min) | % A | % B |
| gradient Flow rate: 1.0 mL/min | 0 | 45 | 55 |
| | 40 | 0 | 100 |
| | 45 | 0 | 100 |
| | 45.1 | 45 | 55 |
| | 60 | 45 | 55 |
| Detection | UV 220 nm | | |
| Column temperature | 40° C. | | |
| Run time | 60 min | | | alternatively, the following equipment and conditions are used:

| Column | YMC Pack Pro-C18, 4.6 mm × 150 mm, 3-µm | | |
|---|---|---|---|
| Solvent | Solvent A: Acetonitrile: Methanol: 10 mM phosphate buffer, pH 7.0 (5:5:90, v:v:v) Solvent B: Acetonitrile: Methanol (80:20, v:v) | | |
| | Time (min) | % A | % B |
| gradient Flow rate: 1.0 mL/min | 0 | 85 | 15 |
| | 35 | 0 | 100 |
| | 45 | 0 | 100 |
| | 45.1 | 85 | 15 |
| | 60 | 85 | 15 |
| Detection | UV 220 nm | | |
| Column temperature | 30° C. | | |
| Run time | 60 min | | |

While the present invention has been described with and in conjunction with the specific embodiments set forth above, these examples are meant to be illustrative and not limiting. Many alternatives, modifications and other variations thereof will be apparent to those of ordinary skill in the art. All such alternatives, modifications and variations are intended to fall within the spirit and scope of the present invention

The invention claimed is:
1. A process for purifying the compound of Formula I

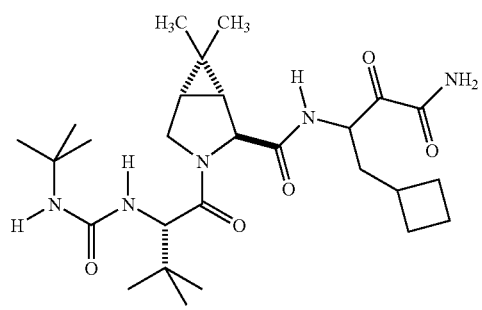

the process comprising:
- (a) extracting an organic phase comprising: (i) the compound of Formula I; and (ii) one or more organic solvents, with an aqueous bisulfite solution, thereby forming an aqueous phase comprising a bisulfite adduct of the compound of Formula I; and
- (b) regenerating the compound of Formula I in a precipitate form by:
  - (i) a process comprising: (1) extracting the aqueous phase containing the bisulfite adduct of the compound of Formula I provided in Step (a) with an organic phase comprising one or more water-miscible organic solvents, thereby forming an organic phase containing the compound of Formula I; and (2) mixing the organic phase provided in extracting Step (b)(i)(1) with water at a temperature suitable to precipitate the compound of Formula I; or
  - (ii) adding the aqueous phase prepared in Step (a) into an organic phase comprising one or more water-miscible organic solvents thereby precipitating the compound of Formula I; or
  - (iii) adding to the aqueous phase provided in Step (a) a carbonyl compound or an oxidant suitable to precipitate the compound of Formula I; or
  - (iv) a process comprising: (1) extracting the aqueous phase provided in Step (a) with an organic phase comprising at least one organic solvent and optionally a carbonyl compound or an oxidant compound; and (2) adding the organic phase obtained in extracting Step (b)(iv)(1) to a solvent or mixture of solvents in which the compound of Formula I is insoluble (an antisolvent) at a temperature suitable to precipitate the compound of Formula I.

2. The process of claim 1 wherein the bisulfite used to form the adduct of the compound of Formula I in Step (a) is sodium bisulfite.

3. The process of claim 1 wherein in Step (a), the organic phase comprises tert-butyl methyl ether and the extraction is carried out at a temperature of from −5° C. to about 10° C.

4. The process of claim 3 wherein the regeneration process used is that described in Step (b)(iv).

5. The process of claim 4 wherein the organic solvent used in Step (b)(iv) is tert-butyl methyl ether.

6. The process of claim 4 wherein the regeneration is carried out in the presence of a carbonyl compound.

7. The process of claim 6 wherein the carbonyl compound is a glyoxylic acid salt.

8. The process of claim 1 wherein, in Step (a), the bisulfite used to form the adduct is sodium bisulfite, the organic solvent is tert-butyl methyl ether and the extraction is carried out at −5° C. to 10° C., and wherein the regeneration process used is that described in Step (b)(iv), and wherein the regeneration process of Step (b)(iv) utilizes tert-butyl methyl ether as the organic phase and wherein a carbonyl compound is present in the form of a glyxoylic acid salt.

9. A process for purifying the compound of Formula I

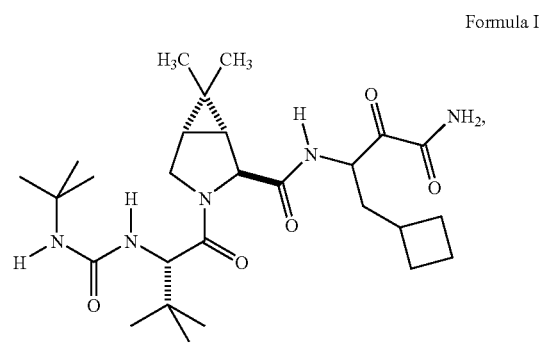

Formula I the process comprising:
- (a) forming an organic phase comprising a bisulfite adduct of the compound of Formula I and one or more organic solvents;
- (b) extracting the bisulfite adduct of the compound of Formula I formed in Step (a) into an aqueous phase; and
- (c) regenerating the compound of Formula I in a precipitate form by:
  - (i) a process comprising: (1) extracting the aqueous phase containing the bisulfite adduct of the compound of Formula I provided in Step (b) with an organic phase comprising one or more water-miscible organic solvents, thereby forming an organic phase containing the compound of Formula I; and (2) mixing the organic phase provided in extracting Step (c)(i)(1) with water at a temperature suitable to precipitate the compound of Formula I; or
  - (ii) adding the aqueous phase prepared in Step (b) into an organic phase comprising one or more water-miscible organic solvents thereby precipitating the compound of Formula I; or
  - (iii) adding to the aqueous phase provided in Step (b) a carbonyl compound or an oxidant suitable to precipitate the compound of Formula I; or
  - (iv) a process comprising: (1) extracting the aqueous phase provided in Step (b) with an organic phase comprising at least one organic solvent and optionally a carbonyl compound or an oxidant compound; and (2) adding the organic phase obtained in extracting Step (c)(iv)(1) to a solvent or mixture of solvents in which the compound of Formula I is insoluble (an antisolvent) at a temperature suitable to precipitate the compound of Formula I.

10. The process of claim 9 wherein the bisulfite used to form the adduct is sodium bisulfite.

11. The process of claim 9 wherein the organic solvent in Step (a) is ethyl acetate or a mixture of ethyl acetate and tert-butyl methyl ether.

12. The process of claim 9 wherein the extraction in Step (b) is carried out at −5° C. to 10° C.

13. The process of claim 9 wherein the regeneration process used is that described in Step (c)(iv).

14. The process of claim 13 wherein the organic solvent used in the regeneration process is tert-butyl methyl ether.

15. The process of claim 14 wherein the regeneration process used is the process of Step (c)(iv), and Step (c)(iv)(1) of the regeneration process is carried out in the presence of a carbonyl compound.

16. The process of claim 15 wherein the carbonyl compound used in the regeneration process is a glyoxylate salt.

17. The process of claim 9 wherein in Step (a), the bisulfite used to form the adduct is sodium bisulfite and the organic solvent is tert-butyl methyl ether, in Step (b) the extraction is carried out at −5° C. to 10° C., and wherein the regeneration process used is that described in Step (c)(iv), and is carried out using tert-butyl methyl ether as the organic solvent in the presence of a glyoxylate salt.

* * * * *